(12) United States Patent
Cundy et al.

(10) Patent No.: US 8,795,725 B2
(45) Date of Patent: Aug. 5, 2014

(54) GABA ANALOG PRODRUG SUSTAINED RELEASE ORAL DOSAGE FORMS

(75) Inventors: Kenneth C. Cundy, Redwood City, CA (US); Srikonda Sastry, Sunnyvale, CA (US); Manshiu Leung, Daily City, CA (US); Balaji V. Kadri, Tampa, FL (US); Paul E. Stach, Plymouth, MN (US)

(73) Assignee: XenoPort, Inc., Santa Clara, CA (US)

( * ) Notice: Subject to any disclaimer, the term of this patent is extended or adjusted under 35 U.S.C. 154(b) by 1315 days.

(21) Appl. No.: 11/269,045

(22) Filed: Nov. 3, 2005

(65) Prior Publication Data

US 2006/0141034 A1 Jun. 29, 2006

Related U.S. Application Data

(60) Provisional application No. 60/625,737, filed on Nov. 4, 2004.

(51) Int. Cl.
*A61K 9/22* (2006.01)

(52) U.S. Cl.
USPC ........................................................ 424/468

(58) Field of Classification Search
None
See application file for complete search history.

(56) References Cited

U.S. PATENT DOCUMENTS

| | | |
|---|---|---|
| 2,996,431 A | 8/1961 | Barry |
| 3,139,383 A | 6/1964 | Neville, Jr. |
| 3,402,240 A | 9/1968 | Cain et al. |
| 3,811,444 A | 5/1974 | Heller et al. |
| 3,845,770 A | 11/1974 | Theeuwes et al. |
| 3,916,899 A | 11/1975 | Theeuwes et al. |
| 3,962,414 A | 6/1976 | Michaels |
| 3,992,518 A | 11/1976 | Chien et al. |
| 4,024,175 A | 5/1977 | Satzinger et al. |
| 4,036,829 A | 7/1977 | Ferres et al. |
| 4,063,064 A | 12/1977 | Saunders et al. |
| 4,066,747 A | 1/1978 | Capozza |
| 4,070,347 A | 1/1978 | Schmitt |
| 4,079,038 A | 3/1978 | Choi et al. |
| 4,083,949 A | 4/1978 | Benedikt |
| 4,087,544 A | 5/1978 | Satzinger et al. |
| 4,088,864 A | 5/1978 | Theeuwes et al. |
| 4,093,709 A | 6/1978 | Choi et al. |
| 4,189,571 A | 2/1980 | Bodor et al. |
| 4,200,098 A | 4/1980 | Ayer et al. |
| 4,285,987 A | 8/1981 | Ayer et al. |
| 4,421,736 A | 12/1983 | Walters |

(Continued)

FOREIGN PATENT DOCUMENTS

| | | |
|---|---|---|
| EP | 0136893 A2 | 4/1985 |
| EP | 0138481 B1 | 4/1985 |

(Continued)

OTHER PUBLICATIONS

Rudnic, Edward et al, Remington's Pharmaceutical Sciences, 1990, Mack Pub. Co., 18th, 1633-1652, 1654-1665, and 1 bibliographic page.*

(Continued)

*Primary Examiner* — Trevor Love
(74) *Attorney, Agent, or Firm* — Polsinelli PC

(57) ABSTRACT

Sustained release oral dosage forms of a gabapentin prodrug, 1-{[(α-isobutanoyloxyethoxy)carbonyl]aminomethyl}-1-cyclohexane acetic acid, are disclosed. The dosage forms are useful for treating or preventing diseases and disorders for which gabapentin is therapeutically effective.

19 Claims, 8 Drawing Sheets

(56) References Cited

U.S. PATENT DOCUMENTS

| | | | |
|---|---|---|---|
| 4,434,153 A | 2/1984 | Urquhart et al. |
| 4,611,056 A | 9/1986 | Guindon et al. |
| 4,721,613 A | 1/1988 | Urguhart et al. |
| 4,752,470 A | 6/1988 | Mehta |
| 4,760,057 A | 7/1988 | Alexander |
| 4,816,263 A | 3/1989 | Ayer et al. |
| 4,820,523 A | 4/1989 | Shtohryn et al. |
| 4,853,229 A | 8/1989 | Theeuwes et al. |
| 4,916,230 A | 4/1990 | Alexander |
| 4,996,058 A | 2/1991 | Sinnreich et al. |
| 5,051,448 A | 9/1991 | Shashoua |
| 5,084,169 A | 1/1992 | Woodruff |
| 5,084,479 A | 1/1992 | Woodruff |
| 5,091,184 A | 2/1992 | Khanna |
| 5,112,598 A | 5/1992 | Biesalski |
| 5,466,811 A | 11/1995 | Alexander |
| 5,556,611 A | 9/1996 | Biesalski |
| 5,563,175 A | 10/1996 | Silverman et al. |
| 5,672,584 A | 9/1997 | Borchardt et al. |
| 5,684,018 A | 11/1997 | Alexander |
| 5,698,155 A | 12/1997 | Grosswald et al. |
| 5,707,663 A | 1/1998 | Ayer et al. |
| 6,001,876 A | 12/1999 | Singh |
| 6,020,370 A | 2/2000 | Horwell et al. |
| 6,024,977 A | 2/2000 | Yatvin et al. |
| 6,028,214 A | 2/2000 | Silverman et al. |
| 6,103,932 A | 8/2000 | Silverman et al. |
| 6,117,906 A | 9/2000 | Silverman et al. |
| 6,127,418 A | 10/2000 | Bueno et al. |
| 6,171,615 B1 | 1/2001 | Roussin et al. |
| 6,310,098 B1 | 10/2001 | Guttuso, Jr. |
| 6,375,987 B1 | 4/2002 | Farah et al. |
| 6,379,700 B2 | 4/2002 | Joachim et al. |
| 6,596,900 B2 * | 7/2003 | Blakemore et al. ........... 562/501 |
| 6,716,453 B1 * | 4/2004 | Harden et al. ................ 424/464 |
| 6,818,787 B2 | 11/2004 | Gallop et al. |
| 6,833,140 B2 | 12/2004 | Cundy et al. |
| 6,972,341 B2 | 12/2005 | Gallop et al. |
| 7,186,855 B2 | 3/2007 | Gallop et al. |
| 2003/0176398 A1 * | 9/2003 | Gallop et al. ................... 514/79 |
| 2004/0198820 A1 | 10/2004 | Cundy et al. |
| 2005/0154057 A1 | 7/2005 | Estrada et al. |
| 2006/0229361 A1 | 10/2006 | Gallop et al. |
| 2007/0010453 A1 | 1/2007 | Gallop et al. |
| 2007/0049626 A1 | 3/2007 | Tran |
| 2007/0049627 A1 | 3/2007 | Tran |

FOREIGN PATENT DOCUMENTS

| | | |
|---|---|---|
| EP | 0458751 A1 | 11/1991 |
| EP | 1178034 A1 | 2/2002 |
| EP | 1201240 A2 | 5/2002 |
| GB | 2362646 A1 | 11/2001 |
| WO | WO 92/09560 | 6/1992 |
| WO | WO 92/09560 A1 | 6/1992 |
| WO | WO 93/18070 A1 | 9/1993 |
| WO | WO 93/23383 | 11/1993 |
| WO | WO 93/23383 A1 | 11/1993 |
| WO | WO 93/25197 A1 | 12/1993 |
| WO | WO 96/38435 A1 | 12/1996 |
| WO | WO 97/29101 | 8/1997 |
| WO | WO 97/29101 A1 | 8/1997 |
| WO | WO 97/33858 | 9/1997 |
| WO | WO 97/33858 A1 | 9/1997 |
| WO | WO 97/33859 | 9/1997 |
| WO | WO 97/33859 A1 | 9/1997 |
| WO | WO 98/04537 A1 | 2/1998 |
| WO | WO 98/06402 A1 | 2/1998 |
| WO | WO 98/17627 | 4/1998 |
| WO | WO 98/17627 A1 | 4/1998 |
| WO | WO 99/00127 A1 | 1/1999 |
| WO | WO 99/08671 | 2/1999 |
| WO | WO 99/08671 A1 | 2/1999 |
| WO | WO 99/21824 | 5/1999 |
| WO | WO 99/21824 A1 | 5/1999 |
| WO | WO 99/31057 | 6/1999 |
| WO | WO 99/31057 A1 | 6/1999 |
| WO | WO 99/31074 A1 | 6/1999 |
| WO | WO 99/31075 | 6/1999 |
| WO | WO 99/31075 A1 | 6/1999 |
| WO | WO 99/37296 | 7/1999 |
| WO | WO 99/37296 A1 | 7/1999 |
| WO | WO 99/61424 | 12/1999 |
| WO | WO 99/61424 A1 | 12/1999 |
| WO | WO 00/15611 A1 | 3/2000 |
| WO | WO 00/23067 | 4/2000 |
| WO | WO 00/23067 A1 | 4/2000 |
| WO | WO 00/31020 | 6/2000 |
| WO | WO 00/31020 A1 | 6/2000 |
| WO | WO 00/50027 | 8/2000 |
| WO | WO 00/50027 A1 | 8/2000 |
| WO | WO 00/73298 A1 | 12/2000 |
| WO | WO 01/42191 A1 | 6/2001 |
| WO | WO 01/54481 A2 | 8/2001 |
| WO | WO 01/62242 A1 | 8/2001 |
| WO | WO 01/90052 A1 | 11/2001 |
| WO | WO 01/90081 A1 | 11/2001 |
| WO | WO 02/00209 | 1/2002 |
| WO | WO 02/00209 A2 | 1/2002 |
| WO | WO 02/04458 A1 | 1/2002 |
| WO | WO 02/04459 A1 | 1/2002 |
| WO | WO 02/10120 A1 | 2/2002 |
| WO | WO 02/18327 A2 | 3/2002 |
| WO | WO 02/28181 A1 | 4/2002 |
| WO | WO 02/28411 A1 | 4/2002 |
| WO | WO 02/28883 A1 | 4/2002 |
| WO | WO 02/32376 A2 | 4/2002 |
| WO | WO 02/34711 A1 | 5/2002 |
| WO | WO 02/38577 A2 | 5/2002 |
| WO | WO 02/42414 A2 | 5/2002 |
| WO | WO 02/062766 A2 | 8/2002 |
| WO | WO 02/096404 A1 | 12/2002 |
| WO | WO 02/100347 | 12/2002 |
| WO | WO 02/100347 A2 | 12/2002 |
| WO | WO 02/100349 A2 | 12/2002 |
| WO | WO 02/100392 A1 | 12/2002 |
| WO | WO 03/000250 A1 | 1/2003 |
| WO | WO 03/005971 A2 | 1/2003 |
| WO | WO 03/011255 A1 | 2/2003 |
| WO | WO 03/035040 A1 | 5/2003 |
| WO | WO 03/103634 A1 | 12/2003 |
| WO | WO 03/104184 A1 | 12/2003 |
| WO | WO 2004/054571 A1 | 7/2004 |
| WO | WO 2004/089289 | 10/2004 |
| WO | WO 2004/089289 A2 | 10/2004 |
| WO | WO 2005/037784 | 4/2005 |
| WO | WO 2005/037784 A2 | 4/2005 |

OTHER PUBLICATIONS

Cundy et al., XP13512 [(±)-1-([(α-Isobutanoyloxyethoxy)carbonyl]aminomethyl)-1-cyclohexane acetic acid], a novel gabapentin prodrug: I. design, synthesis, enzymatic conversion to gabapentin, and transport by intestinal solute transporters. *J. Pharmacol Exp Ther.* 2004, 311,315-23.

Cundy et al, XP13512 [(±)-1-([(α-Isobutanoyloxyethoxy)carbonyl] aminomethyl)-1-cyclohexane acetic acid], a novel gabapentin prodrug: II. Improved oral bioavailability, dose proportionality, and colonic absorption compared with gabapentin in rats and monkeys. *J. Pharmacol Exp Ther.* 2004, 311, 324-33.

Hamdani et al., Physical and thermal characterization of Precirol® and Compritol® as lipophilic glycerides used for the preparation of controlled-release matrix pellets. *International J Pharmaceutics* 2003, 260(1), 47-57.

"Remington's Pharmaceutical Sciences," Lippincott Williams & Wilkins, 889-928, (2005).

Office Action mailed Feb. 26, 2008 in U.S. Appl. No. 11/440,734, filed May 22, 2006.

Office Action mailed Mar. 31, 2008 in U.S. Appl. No. 10/,829,896, filed Apr. 21, 2004.

(56) References Cited

OTHER PUBLICATIONS

International Preliminary Report on Patentability and Written Opinion of the International Searching Authority issued May 8, 2007 for International Application No. PCT1US2005/040127.
International Search Report of the International Searching Authority issued Mar. 30, 2006 for International Application No. PCTIUS2005/040127.
Longer et al., Sustained-Release Drug Delivery Systems, *Remington's Pharmaceutical Sciences*, Chapter 91, 18$^{th}$ Edition (1990): p. 1676-1693.
Czuczwar et al., "The New Generation of GABA Enhancers. Potential in the treatment of epilepsy", *CNS Drugs* (2001), 15(5), 339-350.
Garcia-Borreguero et al., "Treatment of Restless Legs Syndrome With Gabapentin", *Neurology* (2002), 59, 1573-1579.
Guttuso et al., "Gabapentin's Effects on Hot Flashes in Postmenopausal Women: A Randomized Controlled Trial", *Obstet. Gynecol.* (2003), 101(2), 337-345.
Lordi, "Sustained Release Dosage Forms," The Theory and Practice of Industrial Pharmacy, Chapter 14, Lachman et al. eds., 3$^{rd}$ Edition, 1986, 16 pages.
Rowbotham et al., "Gabapentin for the Treatment of Postherpetic Neuralgia A Randomized Controlled Trial", *JAMA* (1998), 280(21), 1837-1842.
U.S. Pharmacopeia, Chapter 711—"Dissolution", 28, 2412-14.
Furlanetto et al., "Study of Formulation Variables Influencing the Drug Release Rate From Matrix Tablets by Experimental Design", *Eur. Jour. of Pharm. And Biopharm.*, 62 (2006), pp. 77-84.
Li et at., "*In vitro* Controlled Release of Sodium Ferulate From Compritol 888 ATO-Based Matrix Tablets", *Intl. Jour. of Pharma.*, 324 (2006), pp. 152-157.
Obaidat et al., "Controlled Release of Tramadol Hydrochloride From Matrices Prepared Using Glyceryl Behenate", *Eur. Jour. of Pharm. and Biopharm.*, 52 (2001), pp. 231-235.
Rinshoiyaku, "Influence of Food Intake on Pharmacokinetics of CS-866 (Olmesaltan Medoxomil), an Angiotensin II Receptor Antagonist", *Medical Online*, 19:11 (2003), pp. 1283-1295.
Alderman, "A Review of Cellulose Ethers in Hydrophilic Matrices or Oral Controlled-Release Dosage Forms," Int. J. Pharm. Tech. & Prod. Mfr. 1984, 5(3) 1-9.
Alexander et al. "Investigation of (Oxodioxolenyl)menthyl Carbamates as Nonchiral Bioreversible Prodrug Moieties for Chiral Amines," Med. Chem. (1996) 39,480-486.
Bamba et al., "Release Mechanisms in Gelforming Sustained Release Preparations," Int. J. Pharm. 1979, 2, 307.
Bryans et al., "3-Substituted GABA Analogs with Central Nervous System Activity: A Review," Med. Res. Rev. 1999, 19, 149-177.
Bryans, et al., Identification of Novel Ligands for the Gabapentin Binding Site on the $\alpha_2\delta$ Subunit of a Calcium Channel and Their Evaluation as Anticonvulsant Agents, J. Med.Chem. 1998, 41, 1838-1845.
Butcher "Carbamate Esters: a Simple, Mild Method of Formation", *Synlett* (1994) 825-826.
Coleman et al., "Polymer Review: A Practical Guide to Polymer Miscibility," Polymers 1990, 31, 1187-1231.
Cundy et al., "XP13512 [($\pm$)-1-([($\alpha$-Isobutanoyloxyethoxy)carbonyl] aminomethyl)-1-cyclohexane Acetic Acid], A Novel Gabapentin Prodrug: I. Design, Synthesis, Enzymatic Conversion to Gabapentin, and Transport by Intestinal Solute Transporters," Journal of Pharmacology and Experimental Therapeutics, 2004, 311, 315-323.
Cundy et al., "XP13512 [($\pm$)-1-([($\alpha$-Isobutanoyloxyethoxy)carbonyl] aminomethyl)-1-cyclohexane Acetic Acid], A Novel Gabapentin Prodrug: II. Improved Oral Bioavailability, Dose Proportionality, and Colonic Absorption Compared with Gabapentin in Rats and Monkeys" Journal of Pharmacology and Experimental Therapeutics, 2004, 311, 324-333.
During et al., "Controlled Release Of Dopamine From A Polymeric Brain Implant: In Vivo Characterization," 1989, Ann. Neurol. 25:351.
Fincher, "Particle Size of Drugs and Its Relationship to Absorption and Activity," J. Pharm. Sci. 1968, 57, 1825-1835.
Gee et al., "The Novel Anticonvulsant Drug, Gabapentin (Neurontin), Binds to the $\alpha_2\delta$ Subunit of a Calcium Channel," J. Biol. Chem. 1996, 271, 5768-5776.
Goodson, "Medical Applications of Controlled Release," vol. 2, pp. 115-138 (1984).
Guttuso et al., "Gabapentin's Effects on Hot Flashes in Postmenopausal Women: A Randomized Controlled Trail," Obstet. Gynecol. 2003, 101, 337-345.
Hamdani et al., "Physical and Thermal Characterization of Precirol and Compritol as Lipophilic Glycerides Used for the Preparation of Controlled-Release Matrix Pellets," International Journal of Pharmaceutics, 2003, 260, 47-57.
Hoes et al., "The Application of Drug-Poymer Conjugates in Chemotherapy," Drug Carrier Systems 1989, 9, 57-10.
Howard et al., "Intercerebral Drug Delivery in Rats with Lesion-Induced Memory Deficits," 1989, J. Neurosurg. 71:105-112.
Jezyk et al., "Transpot of Pregabalin in Rat Intestine and Caco-2 Monolayers," Pharm. Res. 1999, 16, 519-526.
Kayser et al., "Designer Yeast: an Enantioselective Oxidizing Reagent for Organic Synthesis." *SynLett* (1999).
Kronenberg et al. "Thermoregulatory physiology of menopausal hot flashes: a review," Can. J. Physiol. Pharmacol. 1987, 65, 1312-1324.
Langer et al., "Chemical and Physical Structure of Polymers as Carriers for Controlled Release of Bioactive Agents: A Review," J Macromol. Sci. Rev. Macromol Chem. 1983, 23:61-126.
Langer, "New Method of Drug Delivery," 1990, Science 249:1527-1533.
Leong et al., "Polymeric Controlled Drug Delivery" Adv. Drug Delivery Rev. (1987) 1:199-233.
Levy et al., "Inhibition of Calcification of Bioprosthetic Heart Valves by Local Controlled-Release Diphosphonate," Science 1985 228: 190-192.
Loprinzi et al., "Megestrol Acetate for the Prevention of hot Flashes," N. Engl. J. Med. 1994, 331, 347-351.
Lu, "Dimensionless Presentation for Drug release From a Coated Pure Drug Bead: 2 Experiment," Int. J. Pharm (1994) 112, 117-124.
Magnus, "Nonepileptic Uses of Gabapentin," Epilepsia, (40) (Suppl. 6): S66-S72 (1999).
Renz, et al., "100 years of Baeyer-Villiger Oxidations," *Eur.J. Org. Chem.* (1999) 737-750.
Rosoff, *Controlled Release of Drugs* Chap. 2, (1989) pp. 53-95.
Saudek et al., "A Preliminary Trial of the Programmable Implantable Medication System for Insulin Delivery," N. Engl. J. Med. (1989) 321:574-579.
Sefton, "Implantable Pumps," CRC Crit Ref Biomed. Eng. 1987, 14:201.
Stevenson et al., "Colonic Absorption of Antiepileptic Agents," (1997) *Epilepsia* 38(1): 63-7.
Stewart, "Cyclohexanone Monooxygenase: A Useful Reagent for Asymmetric Baeyer-Villiger Reactions," *Current Organic Chemistry* (1998) 2:195-216.
Strukul, "Transition Metal Catalysis in the Baeyer-Villiger Oxidation of Ketones," *Angnew. Chem. Int. Ed.* (1998) 37:1198-1209.
Sun et al., "A General Synthesis of Dioxolenone Prodrug Moieties," *Tetrahedron Letters* (2002) 1161-1164.
Verma et al., "Osmotically Controlled Oral Drug Delivery," Drug Dev. Ind. Pharm., 2000, 26:695-708.

\* cited by examiner

GABA ANALOG PRODRUG SUSTAINED RELEASE ORAL DOSAGE FORMS

This application claims benefit to U.S. Provisional Application No. 60/625,737 filed Nov. 4, 2004, which is incorporated by reference in its entirety.

FIELD

The present disclosure relates to sustained release oral dosage forms of 1-{[(α-isobutanoyloxyethoxy)carbonyl]aminomethyl}-1-cyclohexane acetic acid and to methods of treating or preventing diseases and disorders for which gabapentin is therapeutically effective by administering such dosage forms.

BACKGROUND

1-{[(α-isobutanoyloxyethoxy)carbonyl]aminomethyl}-1-cyclohexane acetic acid, (1), a prodrug of the gamma aminobutyric acid (GABA) analog gabapentin (2), has high bioavailability as gabapentin when dosed either orally or directly into the colon of a mammal (Gallop et al., International Publication No. WO 02/100347; Cundy et al., *J Pharmacol Exp Ther.* 2004, 311:315-323; Cundy et al., *J Pharmacol Exp Ther.* 2004, 311:324-333. The high bioavailability makes compound (1) a valuable component of oral dosage forms (including sustained-release dosage forms) useful for treating or preventing epilepsy, pain (especially, neuropathic pain and muscular and skeletal pain), depression, anxiety, psychosis, faintness attacks, hypokinesia, cranial disorders, neurodegenerative disorders, panic, inflammatory disease (i.e., arthritis), insomnia, gastrointestinal disorders, hot flashes, restless legs syndrome, urinary incontinence, and ethanol withdrawal syndrome.

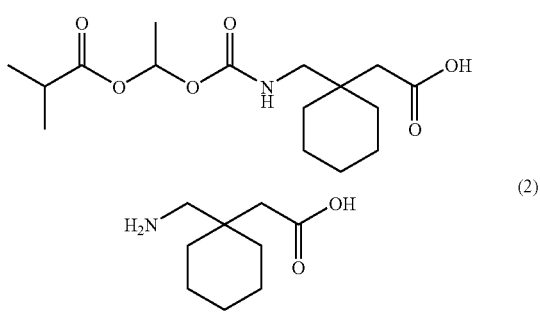

Compound (1), prepared as described in Gallop et al., International Publication No. WO 02/100347 is isolated as a glassy solid after lyophilization from aqueous acetonitrile. The material obtained by this process is partially or wholly amorphous and certain alkali metal salt forms are hygroscopic. More recently, a crystalline form of 1-{[(α-isobutanoyloxyethoxy)carbonyl]aminomethyl}-1-cyclohexane acetic acid and methods for its synthesis have been described (Estrada et al., International Publication No. WO 2005/037784). The crystalline form of compound (1) has improved physicochemical properties useful in pharmaceutical processing and pharmaceutical compositions.

SUMMARY

Disclosed herein are sustained release oral dosage forms of compound (1). In certain embodiments, sustained release oral dosage forms of compound (1) when administered to one or more fasted human patients at a dose of 1-{[(α-isobutanoyloxyethoxy)carbonyl]aminomethyl}-1-cyclohexane acetic acid ranging from about 1100 mg to about 1300 mg provide a gabapentin plasma concentration profile characterized by a $C_{max}$ ranging from about 3 μg/mL to about 6 μg/mL, a $T_{max}$ ranging from about 4 hours to about 7 hours, and an AUC ranging from about 30 μg·hr/mL to about 70 μg·hr/mL; or when administered to one or more fed human patients at a dose of 1-{[(α-isobutanoyloxyethoxy)carbonyl]aminomethyl}-1-cyclohexane acetic acid ranging from about 1100 mg to about 1300 mg provide a gabapentin plasma concentration profile characterized by a $C_{max}$ ranging from about 5 μg/mL to about 8 μg/mL, a $T_{max}$ ranging from about 6 hours to about 11 hours, and an AUC ranging from about 60 μg·hr/mL to about 110 μg·hr/mL.

Dosage forms can be, for example, tablets comprising (a) about 10 wt % to about 80 wt % of compound (1) and (b) about 1 wt % to about 50 wt % of a release rate-modifying polymer, where wt % is based on the total dry weight of the dosage form. Suitable release rate-modifying polymers include glyceryl esters, such as glyceryl monostearate, glyceryl behenate, glyceryl palmitostearate, lauroyl macrogol glyceride, and stearoyl macrogol glyceride. Other suitable release rate-modifying polymers include methacrylate copolymers, ammonioalkyl methacrylate copolymers, and copolymers and combinations thereof.

When administered orally to a patient (i.e., by the patient swallowing the tablet), the dosage forms can provide a curve of concentration of gabapentin in the plasma over time, the curve having the shape and time to maximum plasma concentration ($T_{max}$) shown in FIGS. 1 and 2.

DETAILED DESCRIPTION

Definitions

Figure 1:
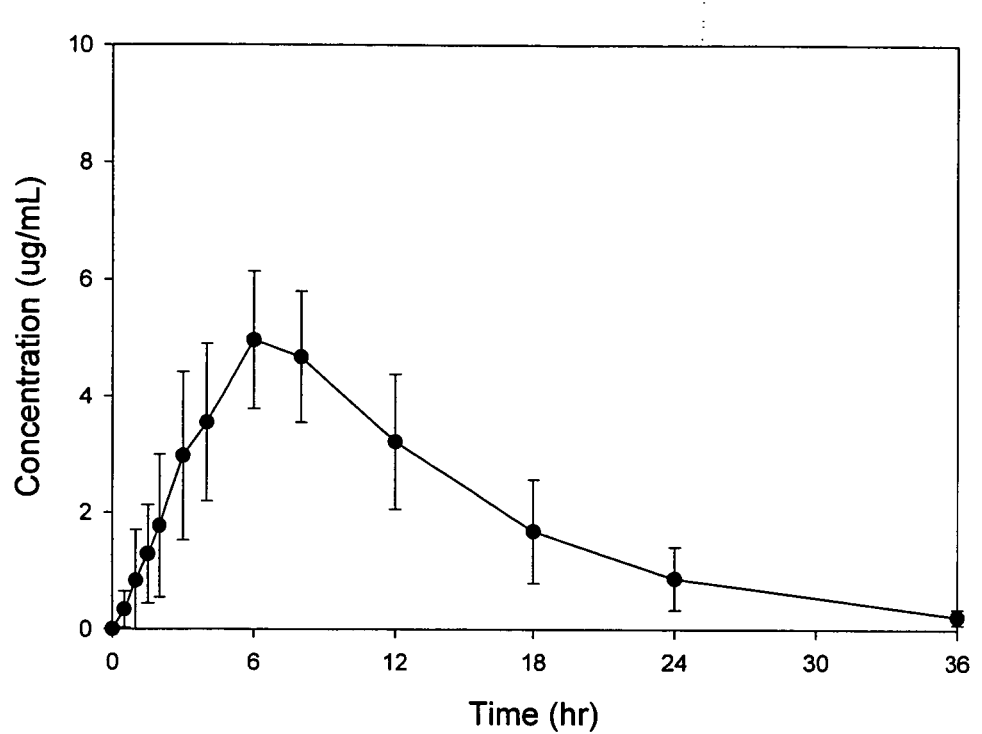
FIG. 1 is a graph of mean concentrations ±SD of gabapentin in plasma after oral administration of sustained release tablets containing compound (1) (2×600 mg) to fasted patients (Treatment A) as described in Example 3.

"AUC" is the area under a curve representing the concentration of a compound or metabolite thereof in a biological fluid in a patient as a function of time following administration of the compound to the patient. In certain embodiments, the compound can be a prodrug and the metabolite can be a drug. Examples of biological fluids include blood and plasma. The AUC can be determined by measuring the concentration of a compound or metabolite thereof in a biological fluid such as the plasma or blood using methods such as liquid chromatography-tandem mass spectrometry (LC/MS/MS), at various time intervals, and calculating the area under the plasma concentration-versus-time curve. Suitable methods for calculating the AUC from a drug concentration-versus-time curve are well known in the art. As relevant to the disclosure here, an AUC for gabapentin can be determined by measuring the concentration of gabapentin in the plasma and/or blood of a patient following oral administration of a dosage form comprising compound (1), 1-{[(α-isobutanoyloxyethoxy)carbonyl]aminomethyl}-1-cyclohexane acetic acid.

"Bioavailability" refers to the rate and amount of a drug that reaches the systemic circulation of a patient following administration of the drug or prodrug to the patient and can be determined by evaluating, for example, the plasma and/or blood concentration-versus-time profile for a compound. Parameters useful in characterizing a plasma and/or blood concentration-versus-time curve include the area under the curve (AUC), the time to peak concentration ($T_{max}$), and the maximum drug concentration ($C_{max}$).

"Bioequivalence" refers to equivalence of the rate and extent of absorption of a drug after administration of equal doses of the drug or prodrug to a patient. As used herein, two plasma or blood concentration profiles are bioequivalent if the 90% confidence interval for the ratio of the mean response of the two profiles is within the limits of 0.8 and 1.25. The mean response includes at least one of the characteristic parameters of a profile such as $C_{max}$, $T_{max}$, and AUC.

"$C_{max}$" is the maximum concentration of a drug in the plasma or blood of a patient following administration of a dose of the drug or prodrug to the patient.

"$T_{max}$" is the time to the maximum concentration ($C_{max}$) of a drug in the plasma or blood of a patient following administration of a dose of the drug or prodrug to the patient.

"Fasted patient" refers to a patient whose stomach is substantially free of food at the time a dose is administered to the patient and for at least 4 hours following administration. The time at which a patient's stomach becomes substantially free of food following a meal can depend on a number of factors including, for example, the size of the meal such as the number of calories, the content of the meal such as the fat content, the health of the patient, and the condition of the patient's gastrointestinal tract. The stomach of a healthy human subject is typically substantially free of food after about 4 to about 8 following ingestion of food. In certain embodiments, a fasted patient does not eat any food (but can ingest any amount of water or clear liquid) from about 10 hours prior to dosing until about 4 hours after dosing, drinks about 250 mL of water about 2 hours and about 1 hour prior to dosing and about 250 mL of water about 2 hours after dosing, eats a lunch about 4 hours after dosing, and eats a dinner about 10 hours after dosing.

"Fed patient" refers to a patient whose stomach contains food. In certain embodiments, a fed patient begins eating a test meal about 30 minutes prior to dosing and completes eating the test meal about 5 minutes prior to dosing, eats a lunch 4 hours after dosing, and eats a dinner about 10 hours after dosing. The test meal comprises a high fat (about 50% of the total number of calories in the test meal) and high calorie (about 1000 total calories) breakfast such as, for example, 2 eggs fried in butter, 2 strips of bacon, 2 slices of wheat toast with butter, 4 ounces of hash brown potatoes, and 8 ounces of whole milk. The test meal contains about 150 protein calories, 250 carbohydrate calories, and about 500 to 600 fat calories.

"Patient" refers to a mammal, for example, a human.

"Pharmaceutically acceptable" refers to approved or approvable by a regulatory agency of the Federal or state government or listed in the U.S. Pharmacopoeia or other generally recognized pharmacopoeia for use in animals and more particularly in humans.

"Pharmaceutically acceptable salt" refers to a salt of a compound of the present disclosure that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine, and the like.

"Preventing" or "prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease).

"Prodrug" refers to a derivative of a drug molecule that requires a transformation within the body to release the active drug. Compound (1) is a prodrug that is metabolized within a patient's body to form the parent drug gabapentin, and hence compound (1) is a prodrug of gabapentin. Compound (1), 1-{[(α-isobutanoyloxyethoxy)carbonyl]aminomethyl}-1-cyclohexane acetic acid, includes pharmaceutically acceptable salts or pharmaceutically acceptable solvates of the free acid form of compound (1), as well as crystalline forms of any of the foregoing.

"Solvate" refers to a molecular complex of a compound with one or more solvent molecules in a stoichiometric or non-stoichiometric amount. Such solvent molecules are those commonly used in the pharmaceutical art, which are known to be innocuous to a recipient, e.g., water, ethanol, and the like. A molecular complex of a compound or moiety of a compound and a solvent can be stabilized by non-covalent intra-molecular forces such as, for example, electrostatic forces, van der Waals forces, or hydrogen bonds. The term "hydrate" refers to a complex where the one or more solvent molecules are water.

"Sustained release" refers to release of compound (1) from a dosage form at a rate effective to achieve a therapeutic or prophylactic concentration of compound (1), or active metabolite thereof, in the systemic blood circulation over a prolonged period of time relative to that achieved by oral administration of an immediate release formulation of compound (1). In some embodiments, release of compound (1) occurs over a period of at least 6 hours, in some embodiments, at least about 12 hours, in some embodiments, at least about 18 hours, and in some embodiments, at least about 24 hours.

"Therapeutically effective amount" means the amount of compound (1) that, when administered to a patient for treating or preventing a disease, is sufficient to effect such treatment or prevention of the disease. The "therapeutically effective amount" will vary depending on the disease and its severity, and the age, weight, etc., of the patient having the disease to be treated or prevented.

"Treating" or "treatment" of any disease or disorder refers, in certain embodiments, to ameliorating the disease or disorder (i.e., arresting or reducing the development of the disease or at least one of the clinical symptoms thereof). In other embodiments "treating" or "treatment" refers to ameliorating at least one physical parameter, which may or may not be discernible by the patient. In certain embodiments, "treating" or "treatment" refers to inhibiting the disease or disorder, either physically, (e.g., stabilization of a discernible symptom), physiologically, (e.g., stabilization of a physical parameter), or both. In certain embodiments, "treating" or "treatment" refers to delaying the onset of the disease or disorder.

"Wt %" refers to the weight of a component or ingredient relative to the total dry weight of a composition or dosage form, e.g., weight percent. For example, a dosage form comprising 40 wt % of compound (1) and that weighs 1000 mg contains 400 mg of compound (1). When referring to a salt and/or solvate of compound (1), the wt % refers to the mass equivalent weight of 1-{[(α-isobutanoyloxyethoxy)carbonyl]aminomethyl}-1-cyclohexane acetic acid forming the pharmaceutically acceptable salt and/or pharmaceutically acceptable solvate of compound (1).

Reference will now be made in detail to certain embodiments of dosage forms and methods. The disclosed embodiments are not intended to be limiting of the claims. To the contrary, the claims are intended to cover all alternatives, modifications, and equivalents of the disclosed embodiments.

Sustained Release Oral Dosage Forms

Although certain embodiments of the present disclosure provide sustained release oral dosage forms in the form of tablets, those skilled in the art of sustained release oral dosage forms will appreciate that other sustained release oral dosage forms such as powders, particulates, sachets, liquid suspensions, and/or capsules for reconstitution can also be used. In certain embodiments, a dosage form can be a tablet, which can be of any shape suitable for oral administration of a drug, such as spheroidal, cube-shaped oval, or ellipsoidal. A tablet can comprise a unit dose of compound (1), or in the case of a mini-tablet, which comprises less than a unit dose, mini-tablets can be filled into capsules to provide a unit dose. In certain embodiments, a tablet can be a multilayer tablet in which different layers contain different particle populations and/or different excipients that affect the release properties of compound (1) from each tablet layer. Examples of tablets include disintegrating tablets, fast dissolving tablets, effervescent tablets, fast melt tablets, chewable tablets, crushable tablets, and mini-tablets. Generally, tablet dosage forms can be compressed to a hardness of at least about 15 kiloponds (kp) (equal to 147.1 Newtons). Dosage forms can be prepared in a manner known in the art and can further include pharmaceutically acceptable excipients, as appropriate.

In some embodiments, a sustained release oral dosage form comprises (a) about 10 wt % to about 80 wt % of compound (1) and (b) about 1 wt % to about 30 wt % of a release rate-modifying polymer.

In some embodiments, a sustained release oral dosage form comprises (a) about 10 wt % to about 80 wt % of compound (1) and (b) about 1 wt % to about 50 wt % of a release rate-modifying polymer.

In some embodiments, a sustained release oral dosage form comprises (a) about 30 wt % to about 75 wt % of compound (1) and (b) about 1 wt % to about 50 wt % of a release rate-modifying polymer.

In some embodiments, a sustained release oral dosage form comprises (a) about 40 wt % to about 65 wt % of compound (1) and (b) about 1 wt % to about 50 wt % of a release rate-modifying polymer.

In some embodiments, a sustained release oral dosage form comprises (a) about 50 wt % to about 60 wt % of compound (1) and (b) about 20 wt % to about 50 wt % of a release rate-modifying polymer.

Dosage forms of the present disclosure are matrix systems in which compound (1) is homogenously dispersed in a release-rate modifying polymer and optionally excipients. Matrix systems are well-known in the are as described, for example, in "Handbook of Pharmaceutical Controlled Release Technology," ed. D. L. Wise, Marcel Dekker, Inc. (2000), and "Treatise on Controlled Drug Delivery, Fundamentals, Optimization, and Applications," ed. A. Kydonieus, Marcel Dekker, Inc. (1992). Release rate-modifying polymers can retard the release of the drug from a dosage form. Suitable release rate-modifying polymers include, but are not limited to, pH sensitive polymers, pH insensitive polymers, hydrophilic polymers that have a high degree of swelling when in contact with water or aqueous media, polymers that form a gel on contact with water or aqueous media, polymers that exhibit both swelling and gelling characteristics in contact with water or aqueous media, fatty compounds such as waxes, and biodegradable polymers.

In certain embodiments, a release rate-modifying polymer can be a pH sensitive polymer such as acrylic acid and methacrylic acid polymers and copolymers, methyl methacrylate copolymers, ethoxyethyl methacrylates, cyanoethyl methacrylate, poly(acrylic acid), poly(methacrylic acid), methacrylic acid alkylamide copolymer, poly(methyl methacrylate), polymethacrylate, poly(methyl methacrylate) copolymers, polyacrylamide, aminoalkyl methacrylate copolymer, poly(methacrylic acid anhydride), glycidyl methacrylate co-polymers, ammonioalkyl methacrylate copolymers, and combinations of any of the foregoing. In certain embodiments, a pH-dependent polymer can be a copolymer synthesized from diethylaminoethyl methacrylate and other neutral methacrylic esters, also known as methacrylic acid copolymers or polymer methacrylates, commercially available as Eudragit (Rohm Pharma).

In certain embodiments, a pH insensitive polymer is an ammonioalkyl methacrylate copolymer such as Eudragit™ RS and Eudragit™ RL, which are acrylic resins comprising copolymers of acrylic and methacrylic acid esters with a low content of quaternary ammonium groups.

Examples of hydrophilic release rate-modifying polymers that exhibit a high degree of swelling include cross-linked sodium carboxymethylcellulose, cross-linked hydroxypropylcellulose, high-molecular weight hydroxypropylmethylcellulose, carboxymethylamide, potassium methacrylatedivinylbenzene co-polymer, polymethylmethacrylate, polyvinylpyrrolidone, high-molecular weight polyvinylalcohols, methyl cellulose, vinyl acetate copolymers, and the like.

Examples of release rate-modifying polymers that gel in contact with water include methylcellulose, carboxymethylcellulose, low-molecular weight hydroxypropylmethylcellulose, low-molecular weight polyvinylalcohols, polyoxyethyleneglycols, non-cross linked polyvinylpyrrolidone, xanthan gum, and the like.

Examples of release rate-modifying polymers that exhibit both swelling and gelling properties include medium-viscosity hydroxypropylmethylcellulose and medium-viscosity polyvinylalcohols.

In certain embodiments, the release rate-modifying polymer is a glyceryl ester such as glyceryl monostearate, glyceryl behenate, glyceryl palmitostearate, lauroyl macrogol glyceride, stearoyl macrogol glyceride, or a combination of any of the foregoing. In certain embodiments, the release rate-modifying polymer is glyceryl behenate. Other fatty and/or waxy release rate-modifying polymers include lauryl alcohol, myristyl alcohol, stearyl alcohol, cetyl alcohol, cetostearyl alcohol, palmitoyl alcohol, ouricury wax, hydrogenated vegetable oil, candelilla wax, esparto wax, stearic acid, paraffin wax, beeswax, glycowax, castor wax, and carnauba wax.

Examples of bioerodible polymers include collagen, gelatin, polyvinyl alcohols, polyorthoesters, polyacetyls, polyorthocarbonates, polyamides, polyaminoacids, polyesters, polylactic acids, polyglycolic acids, polycarbohydrates, polyorthoesters, polyorthocarbonates, polyacetyls, polyanhydrides, polydehydropyrans, polydioxinones, and the like.

Other suitable release-modifying polymers that can be incorporated into a dosage from of the present disclosure include hydrocolloids such as natural or synthetic gums, carbohydrate-based substances such as acacia, gum tragacanth, locust bean gum, guar gum, agar, pectin, carageenin, soluble and insoluble alginates, carboxypolymethylene, casein, zein, polyethylene oxide, maleic anhydride/methyl vinyl ether copolymers, and proteinaceous substances such as gelatin.

A release rate-modifying polymer can be used alone or in combination with one or more other release rate-modifying polymers and/or can be a copolymer of more than one release rate-modifying polymer.

Formulations of compound (1) and one ore more release-modifying polymers can be prepared using standard techniques well known in the art such as wet granulation, fluid-bed granulation, dry granulation, and direct compression (see "Remington's Pharmaceutical Sciences," Lippincott Williams & Wilkins, 889-928, (2005). For example, matrix formulations can be prepared by dry blending a release-modifying polymer, filler, compound (1), and excipients followed by granulating the mixture using an alcohol until proper granulation is obtained. The granulation can be done by methods known in the art. The wet granules can be dried in a fluid bed dryer, sifted, and ground to an appropriate size. Lubricating agents can be mixed with the dried granulation to obtain a final formulation. In certain embodiments, such formulations can be compressed into a tablet dosage form by methods well known in the art.

In certain embodiments, the amount of compound (1) in a dosage form ranges from about 50 mg to about 800 mg, in certain embodiments, from about 100 mg to about 800 mg, and in certain embodiments, from about 300 mg to about 700 mg. For dosage forms comprising a pharmaceutically acceptable salt and/or solvate of compound (1), the amount of compound (1) in a dosage form refers to the mass equivalent weight of compound (1). The amount or loading of compound (1) contained in a dosage form can depend on the particular condition being treated and on the amount of gabapentin generated from the prodrug loading following absorption.

In addition to compound (1) and the release rate-modifying polymers described herein, a dosage form can also comprise one or more pharmaceutically acceptable excipients such as surfactants, lubricants, diluents, anti-adherents, glidants, buffers, dyes, wetting agents, emulsifying agents, pH buffering agents, stabilizing agents, thickening agents, disintegrants, and coloring agents. Such excipients include starch, sugars, gelatin, malt, rice, flour, chalk, silica gel, sodium stearate, glycerol monostearate, talc, sodium chloride, glycerol, propylene glycol, water, ethanol, and the like.

Diluents can be added to increase the bulk to make a dosage form a practical size for compression. Examples of useful diluents include dibasic calcium phosphate, dibasic calcium phosphate dihydrate, calcium sulfate, dicalcium phosphate, tricalcium phosphate, lactose, cellulose including microcrystalline cellulose, kaolin, mannitol, sodium chloride, dry starch, pregelatinized starch, compressible sugar, mannitol, and combinations of any of the foregoing. In certain embodiments, a diluent is selected from dibasic calcium phosphate and microcrystalline cellulose. In certain embodiments wherein the diluent is dibasic calcium phosphate, a dosage form can comprise an amount of diluent ranging from about 30 wt % to about 50 wt %, and in certain embodiments, from about 35 wt % to about 45 wt %. In certain embodiments wherein the diluent is microcrystalline cellulose, a dosage form can comprise an amount of diluent ranging from about 5 wt % to about 20 wt %, and in certain embodiments, from about 10 wt % to about 16 wt %.

Glidants can be included in dosage forms of the present disclosure to reduce sticking effects during processing, film formation, and/or drying. Examples of useful glidants include talc, magnesium stearate, glycerol monostearate, colloidal silicon dioxide, precipitated silicon dioxide, and combinations of any of the foregoing. In certain embodiments, a glidant is colloidal silicon dioxide. A dosage form can comprise less than about 2 wt % of a glidant, and in certain embodiments, less than about 1 wt % of a glidant.

Lubricants and anti-adherents can be included in dosage forms of the present disclosure to aid in processing. Examples of useful lubricants and/or anti-adherents include calcium stearate, glyceryl behenate, glyceryl monostearate, magnesium stearate, mineral oil, polyethylene glycol, sodium stearyl fumarate, sodium lauryl sulfate, sodium dodecyl sulfate, stearic acid, talc, hydrogenated vegetable oil, zinc stearate, and combinations of any of the foregoing. In certain embodiments, the lubricant is glyceryl monostearate. In certain embodiments, a lubricant is magnesium stearate. A dosage form can comprise an amount of lubricant and/or anti-adherent ranging from about 1 wt % to about 13 wt %, and in certain embodiments, from about 4 wt % to about 10 2 t %.

Examples of surfactants useful in dosage forms of the present disclosure include pharmaceutically acceptable anionic surfactants, cationic surfactants, amphoteric (amphiphatic/amphiphilic) surfactants, non-ionic surfactants, polyethyleneglycol esters or ethers, and combinations of any of the foregoing. Examples of suitable pharmaceutically acceptable anionic surfactants include monovalent alkyl carboxylates, acyl lactylates, alkyl ether carboxylates, N-acyl sarcosinates, polyvalent alkyl carbonates, N-acyl glutamates, fatty acid-polypeptide condensates, sulfuric acid esters, alkyl sulfates such as sodium lauryl sulfate and sodium dodecyl sulfate, ethoxylated alkyl sulfates, ester linked sulfonates such as docusate sodium and dioctyl sodium succinate, alpha olefin sulfonates, or phosphated ethoxylated alcohols. Examples of suitable pharmaceutically acceptable cationic surfactants include monoalkyl quaternary ammonium salts, dialkyl quaternary ammonium compounds, amidoamines, and aminimides. Examples of suitable pharmaceutically acceptable amphoteric surfactants include, N-substituted alkyl amides, N-alkyl betaines, sulfobetaines, and N-alkyl-6-aminopropionates. Examples of suitable pharmaceutically acceptable polyethyleneglycol esters or ethers include polyethoxylated castor oil, polyethoxylated hydrogenated castor oil, and hydrogenated castor oil. In certain embodiments, a surfactant is selected from sodium lauryl sulfate and sodium dodecyl sulfate. In certain embodiments, a dosage form can comprise less than about 3 wt % of a surfactant, and in certain embodiments, less than about 2 wt % of a surfactant.

Dosage forms of the present disclosure, such as tablet dosage forms, can further comprise one or more coatings. The purpose of the one or more additional coatings can be for physical protection, aesthetics, ease in swallowing, identification, and/or to facilitate further processing of the particles. While certain coatings may be applied to modify or affect the release of compound (1) from the dosage form in the gastrointestinal tract, others may have no such effect. A coating can be impermeable to moisture or moisture permeable. A moisture permeable exterior tablet coating can be useful for maintaining low moisture content in a dosage form that is packaged in the presence of a desiccant and can thereby enhance, for example, the storage stability of the dosage form. These additional coatings can be applied to a dosage form of the present disclosure by methods known to those skilled in the art. Examples of materials useful in coatings for physical protection include permeable or soluble materials such as hydroxypropyl methylcellulose, hydroxypropyl cellulose, hydroxypropyl ethylcellulose, and xanthan gum. Examples of materials useful in coatings to facilitate further processing include talc, colloidal silica, polyvinyl alcohol, titanium dioxide, micronized silica, fumed silica, glycerol monostearate, magnesium trisilicate, and magnesium stearate. A coating can comprise a single material or a combination of more than one material including any of those disclosed herein.

A dosage form of the present disclosure can be substantially free of lactam side products formed by intramolecular cyclization of compound (1) and/or gabapentin. A dosage form is preferably stable to extended storage (more preferably, greater than one year) without substantial lactam formation (preferably, less than 0.5% lactam by weight, more preferably, less than 0.2% lactam by weight, most preferably, less than 0.1% lactam by weight).

In certain embodiments, compound (1) in the dosage form is the crystalline form disclosed in Estrada et al., U.S. Patent Application Publication US 2005/0154057 published Jul. 14, 2005.

Figure 2:
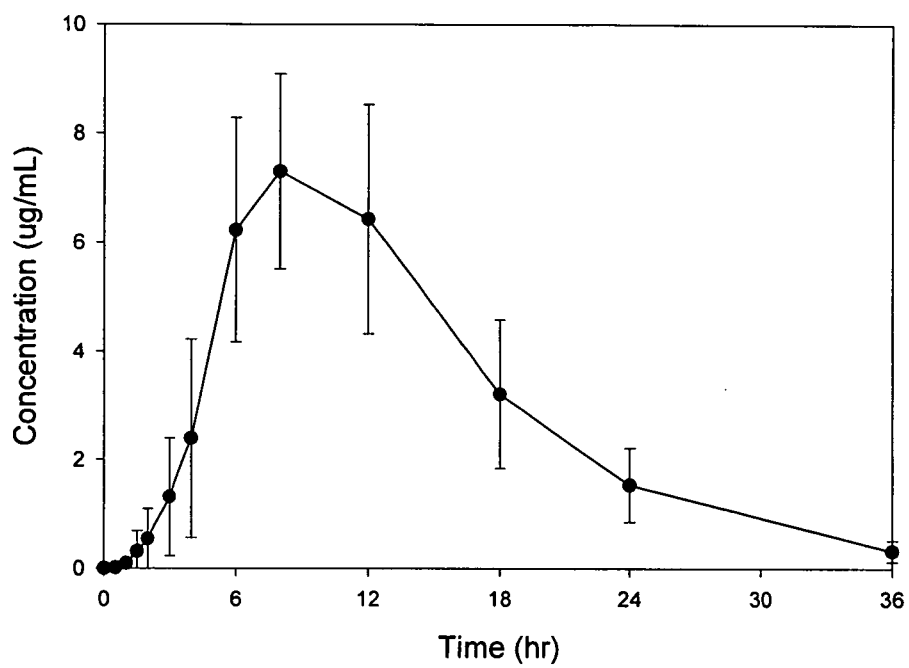
FIG. 2 is a graph of mean concentrations ±SD of gabapentin in plasma after oral administration of sustained release tablets containing compound (1) (2×600 mg) to fed patients (Treatment B) as described in Example 3.

When administered orally to a patient (i.e., by the patient swallowing the tablet), a dosage form of the present disclosure can provide a profile of gabapentin concentration in the plasma or blood over time for a dosage form having the compositions and loadings described in Example 1, the gabapentin plasma concentration profile has the shape, magnitude, and AUC shown in FIGS. 1 and 2 for fasted and fed human patients, respectively, following administration of compound (1) to a patient. These profiles are different than profiles obtained following administration of gabapentin alone. One important difference is the time ($T_{max}$) to reach the maximum blood concentration ($C_{max}$). In fasted patients, the $T_{max}$ for a sustained release oral dosage form of the present disclosure is greater than about 4 hrs. In fed patients, the $T_{max}$ for a sustained release oral dosage form is greater than about 6 hrs. In contrast, the $T_{max}$ following administration of gabapentin alone to fasted and fed patients is about 2-4 hrs. Another important advantage of sustained release oral dosage forms of the present disclosure is the bioavailability of the gabapentin metabolite. At a loading dose of 1200 mg of compound (1), a dosage form of the present disclosure can provide at least 20% higher gabapentin bioavailability, and in certain embodiments at least 25% higher bioavailability, in fasted patients compared to administration of an equimolar dose of gabapentin. At a loading dose of 1200 mg of compound (1), a sustained release oral dosage form of the present disclosure can provide at least 50% higher gabapentin bioavailability, and in certain embodiments at least 100% higher bioavailability, in fed patients compared to administration of an equimolar dose of gabapentin.

In certain embodiments, a sustained release oral dosage form of 1-{[(α-isobutanoyloxyethoxy)carbonyl]aminomethyl}-1-cyclohexane acetic acid, when administered to one or more fasted human patients at a dose of 1-{[(α-isobutanoyloxyethoxy)carbonyl]aminomethyl}-1-cyclohexane acetic acid ranging from about 1100 mg to about 1300 mg, can provide a gabapentin plasma concentration profile characterized by a $C_{max}$ ranging from about 3 µg/mL to about 6 µg/mL, a $T_{max}$ ranging from about 4 hours to about 7 hours, and an AUC ranging from about 30 µg·hr/mL to about 70 µg·hr/mL.

In certain embodiments, a sustained release oral dosage form of 1-{[(α-isobutanoyloxyethoxy)carbonyl]aminomethyl}-1-cyclohexane acetic acid, when administered to one or more fed human patients at a dose of 1-{[(α-isobutanoyloxyethoxy)carbonyl]aminomethyl}-1-cyclohexane acetic acid ranging from about 1100 mg to about 1300 mg, can provide a gabapentin plasma concentration profile characterized by a $C_{max}$ ranging from about 5 µg/mL to about 8 µg/mL, a $T_{max}$ ranging from about 6 hours to about 11 hours, and an AUC ranging from about 60 µg·hr/mL to about 110 µg·hr/mL.

In certain embodiments, a sustained release oral dosage form of 1-{[(α-isobutanoyloxyethoxy)carbonyl]aminomethyl}-1-cyclohexane acetic acid, when administered to a population of fasted human patients at a dose of 1-{[(α-isobutanoyloxyethoxy)carbonyl]aminomethyl}-1-cyclohexane acetic acid ranging from about 1100 mg to about 1300 mg, can provide a gabapentin plasma concentration profile characterized by a mean $C_{max}$ ranging from about 3 µg/mL to about 6 µg/mL, a mean $T_{max}$ ranging from about 4 hours to about 7 hours, and a mean AUC ranging from about 30 µg||hr/mL to about 70 µg·hr/mL, and when administered to a population of fed human patients at a dose of 1-{[(α-isobutanoyloxyethoxy)carbonyl]aminomethyl}-1-cyclohexane acetic acid ranging from about 1100 mg to about 1300 mg can provide a gabapentin plasma concentration profile characterized by a mean $C_{max}$ ranging from about 5 µg/mL to about 8 µg/mL, a mean $T_{max}$ ranging from about 6 hours to about 11 hours, and a mean AUC ranging from about 60 µg·hr/mL to about 110 µg·hr/mL.

In certain embodiments, oral administration of two sustained release oral dosage forms, each dosage form comprising 600 mg of 1-{[(α-isobutanoyloxyethoxy)carbonyl]aminomethyl}-1-cyclohexane acetic acid, to one or more fasted human patients can provide a gabapentin plasma concentration profile characterized by a $C_{max}$ ranging from about 3 µg/mL to about 6 µg/mL, a $T_{max}$ ranging from about 4 hours to about 7 hours, and an AUC ranging from about 30 µg·hr/mL to about 70 µg·hr/mL.

In certain embodiments, oral administration of two sustained release oral dosage forms, each dosage form comprising 600 mg of 1-{[(α-isobutanoyloxyethoxy)carbonyl]aminomethyl}-1-cyclohexane acetic acid, to one or more fed human patients can provide a gabapentin plasma concentration profile characterized by a $C_{max}$ ranging from about 5 µg/mL to about 8 µg/mL, a $T_{max}$ ranging from about 6 hours to about 11 hours, and an AUC ranging from about 60 µg·hr/mL to about 110 µg·hr/mL.

In certain embodiments, oral administration of two sustained release oral dosage forms, each dosage form comprising 600 mg of 1-{[(α-isobutanoyloxyethoxy)carbonyl]aminomethyl}-1-cyclohexane acetic acid, to a population of fasted human patients can provide a gabapentin plasma concentration profile characterized by a $C_{max}$ ranging from about 3 µg/mL to about 6 µg/mL, a $T_{max}$ ranging from about 4 hours to about 7 hours, and an AUC ranging from about 30 µg·hr/mL to about 70 µg·hr/mL., and oral administration of two sustained release oral dosage forms, each dosage form comprising 600 mg of 1-{[(α-isobutanoyloxyethoxy)carbonyl]aminomethyl}-1-cyclohexane acetic acid, to a population of fed human patients can provide a gabapentin plasma concentration profile characterized by a mean $C_{max}$ ranging from about 5 µg/mL to about 8 µg/mL, a mean $T_{max}$ ranging from about 6 hours to about 11 hours, and a mean AUC ranging from about 60 µg·hr/mL to about 110 µg·hr/mL.

Dosage forms of the present disclosure include dosage forms that are bioequivalent to the dosage forms disclosed herein, in terms of both rate and extent of absorption, for example as defined by the U.S. Food and Drug Administration and discussed in "Guidance for Industry—Bioavailability and Bioequivalence Studies for Orally Administered Drug Products" (2003).

In certain embodiments, a sustained release oral dosage form of 1-{[(α-isobutanoyloxyethoxy)carbonyl]aminomethyl}-1-cyclohexane acetic acid, when administered to one or more fasted human patients at a dose of 1-{[(α-isobutanoyloxyethoxy)carbonyl]aminomethyl}-1-cyclohexane acetic acid ranging from about 1100 mg to about 1300 mg provides a gabapentin plasma concentration profile bioequivalent to the profile shown in FIG. 1, or when administered to one or more fed human patients can provide a gabapentin plasma concentration profile bioequivalent to the profile shown in FIG. 2.

In certain embodiments, a sustained release oral dosage form of 1-{[(α-isobutanoyloxyethoxy)carbonyl]aminomethyl}-1-cyclohexane acetic acid, when administered to one or more fasted human patients at a dose of 1-{[(α-isobutanoyloxyethoxy)carbonyl]aminomethyl}-1-cyclohexane acetic acid ranging from about 1100 mg to about 1300 mg provides a gabapentin plasma concentration profile bioequivalent to the profile shown in FIG. 1, and when administered to one or more fed human patient can provide a gabapentin plasma concentration profile bioequivalent to the profile shown in FIG. 2.

In certain embodiments, oral administration of two sustained release oral dosage forms, each dosage form comprising 600 mg of 1-{[(α-isobutanoyloxyethoxy)carbonyl]aminomethyl}-1-cyclohexane acetic acid, to one or more fasted human patients can provide a gabapentin plasma concentration profile bioequivalent to the profile shown in FIG. 1, or oral administration of the same dosage form to one or more fed human patients can provide a gabapentin plasma concentration profile bioequivalent to the profile shown in FIG. 2.

In certain embodiments, oral administration of two sustained release oral dosage forms, each dosage form comprising 600 mg of 1-{[(α-isobutanoyloxyethoxy)carbonyl]aminomethyl}-1-cyclohexane acetic acid, to one or more fasted human patients can provide a gabapentin plasma concentration profile bioequivalent to the profile shown in FIG. 1, and oral administration of the same dosage form to one or more fed human patients can provide a gabapentin plasma concentration profile bioequivalent to the profile shown in FIG. 2.

Following oral administration, dosage forms of the present disclosure can provide a therapeutic or prophylactic concentration of gabapentin in the blood and/or plasma of a patient for a time period of at least about 6 hours, in certain embodiments, for at least about 12 hours, in certain embodiments, for at least about 18 hours, and in certain embodiments for at least about 24 hours. A therapeutically or prophylactically effective concentration of gabapentin in the blood and/or plasma of a patient can depend on a number of factors including, for example, the disease being treated, the severity of the disease, the weight of the patient, the health of the patient, and so forth.

In certain embodiments, dosage forms of the present disclosure can be administered twice per day, and in certain embodiments, once per day.

Therapeutic Uses

Sustained release oral dosage forms of the present disclosure can be administered to a patient suffering from any disease or disorder for which the parent drug, gabapentin, is known or hereafter discovered to be therapeutically effective. Conditions for which gabapentin has been prescribed, and hence for which the dosage forms disclosed herein are also effective, include epilepsy, depression, anxiety, psychosis, cognition, schizophrenia, faintness attacks, hypokinesia, cranial disorders, neurodegenerative disorders, panic, pain (especially, neuropathic pain (e.g., post-herpetic neuralgia), muscular and skeletal pain), restless legs syndrome, hot flashes, urinary incontinence, inflammatory disease (i.e., arthritis), insomnia, gastrointestinal disorders, alcohol/cocaine addiction, ethanol withdrawal syndrome, vulvodynia, premature ejaculation, and as a glutamatergic. The dosage forms can also be administered to a patient as a preventative measure against the above-listed diseases or disorders. Thus, the dosage forms can be administered as a preventative measure to a patient having a predisposition for epilepsy, depression, anxiety, psychosis, faintness attacks, hypokinesia, cranial disorders, neurodegenerative disorders, panic, pain (especially, neuropathic pain and muscular and skeletal pain), inflammatory disease (i.e., arthritis), insomnia, gastrointestinal disorders, ethanol withdrawal syndrome, premature ejaculation, and vulvodynia. Accordingly, the dosage forms may be used for the prevention of one disease or disorder and concurrently for treating another disease or disorder (e.g., prevention of psychosis while treating gastrointestinal disorders; prevention of neuropathic pain while treating ethanol withdrawal syndrome). The dosage forms may be used in combination with other drugs such as antiviral drugs during an initial viral infection to prevent or reduce subsequent occurrence of neuropathic disorders. Additionally, the dosage forms may be used in combination with other drugs that are themselves known to cause neuropathic disorders as a side effect, thereby preventing or reducing the occurrence of said side effects.

The suitability of the dosage forms in treating or preventing the above-listed diseases and conditions may be determined by methods described in the art (See, e.g., Satzinger et al., U.S. Pat. No. 4,024,175; Satzinger et al., U.S. Pat. No. 4,087,544; Woodruff, U.S. Pat. No. 5,084,169; Silverman et al., U.S. Pat. No. 5,563,175; Singh, U.S. Pat. No. 6,001,876; Horwell et al., U.S. Pat. No. 6,020,370; Silverman et al., U.S. Pat. No. 6,028,214; Horwell et al., U.S. Pat. No. 6,103,932; Silverman et al., U.S. Pat. No. 6,117,906; Silverman, International Publication No. WO 92/09560; Silverman et al., International Publication No. WO 93/23383; Horwell et al., International Publication No. WO 97/29101, Horwell et al., International Publication No. WO 97/33858; Horwell et al., International Publication No. WO 97/33859; Bryans et al., International Publication No. WO 98/17627; Guglietta et al., International Publication No. WO 99/08671; Bryans et al., International Publication No. WO 99/21824; Bryans et al., International Publication No. WO 99/31057; Magnus-Miller et al., International Publication No. WO 99/37296; Bryans et al., International Publication No. WO 99/31075; Bryans et al., International Publication No. WO 99/61424; Pande, International Publication No. WO 00/23067; Bryans, International Publication No. WO 00/31020; Bryans et al., International Publication No. WO 00/50027; Bryans et al, International Publication No. WO 02/00209; Tran, U.S. Application Ser. No. 60/711,477 filed Aug. 5, 2005; and Tran, U.S. Application Ser. No. 60/710,963 filed Aug. 5, 2005).

Dosing

The amount of compound (1) that will be effective in the treatment of a particular disease, disorder, or condition disclosed herein will depend, at least in part, on the nature of the disorder or condition, and can be determined by standard clinical techniques known in the art as previously described. In addition, in vitro or in vivo assays may optionally be employed to help identify optimal dosage ranges. The amount of the prodrug administered will, of course, depend on, among other factors, the subject having the disease being treated, the weight of the subject, the severity of the affliction, the manner of administration, and the judgment of the prescribing physician.

In some embodiments, sustained release oral dosage forms are adapted to be administered to a patient 1-3 times per day. In other embodiments, sustained release oral dosage forms are adapted to be administered to a patient 1-2 times per day. Dosing may be provided alone or in combination with other drugs and may continue as long as required for effective treatment or prevention of the disease or disorder.

Suitable dosage ranges for oral administration of gabapentin are generally about 100 mg/day to 3600 mg/day and the dose of compound (1) or pharmaceutically acceptable salts or pharmaceutically acceptable solvates thereof may be adjusted to provide an equivalent molar quantity of gabapentin. Dosage ranges may be readily determined by methods known to those skilled in the art.

The following examples further illustrate sustained release oral dosage forms, methods and materials used in making sustained release oral dosage forms and the results achieved upon administration of the dosage form to patients.

EXAMPLES

Example 1

Sustained release oral dosage form tablets containing compound (1) were made having the ingredients shown in Table 1:

TABLE 1

| Ingredient | Manufacturer | Amount/ Tablet (mg/ tablet) | Composition (wt %) | Ingredient Category |
|---|---|---|---|---|
| Compound (1) | XenoPort (Santa Clara, CA) | 600.00 | 45.80 | Prodrug |
| Dibasic Calcium Phosphate, USP | Rhodia (Chicago, IL) | 518.26 | 39.56 | Diluent |
| Glyceryl Behenate, NF | Gattefosse (Saint Pirest, Cedex, France) | 60.05 | 4.58 | Lubricant/ Release controlling agent |
| Talc, USP | Barrett Minerals (Mount Vernon, IN) | 80.02 | 6.11 | Anti-adherent |
| Colloidal Silicon Dioxide, NF | Cabot (Tuscola, IL) | 5.43 | 0.41 | Glidant |
| Sodium Lauryl Sulfate, NF | Fisher (Fairlawn, NJ) | 24.00 | 1.84 | Surfactant |
| Magnesium Stearate, NF | Mallinckrodt (Phillipsburg, NJ) | 22.22 | 1.69 | Lubricant |
| Total | | 1310.00 | 100 | |

The tablets were made according to the following steps. Compound (1), dibasic calcium phosphate, glyceryl behenate, talc, and colloidal silicon dioxide were weighed out, screened through a #20 mesh screen and mixed in a V-blender for 15 minutes. The slugging portion of the sodium lauryl sulfate was weighed and passed through a #30 mesh screen. The slugging portion of the magnesium stearate was weighed and passed through a #40 mesh screen. Screened sodium lauryl sulfate and magnesium stearate were added to the V-blender and blended for 5 minutes. The blend was discharged and compressed into slugs of approximately 400 mg weight on a tablet compression machine. The slugs were then passed through a Comil 194 Ultra mill (Quadro Engineering, Inc., Millburn, N.J.) to obtain the milled material for further compression. The tableting portion of the sodium lauryl sulfate was weighed and passed through a #30 mesh screen. The tableting portion of the magnesium stearate was weighed and passed through a #40 mesh screen. The milled material and the tableting portions of the sodium lauryl sulfate and magnesium stearate were added to the V-blender and blended for 3 minutes. The blended material was discharged and compressed to form tablets having a total weight of 1310 mg and a compound (1) loading of 600 mg (45.8 wt %). The tablets had a mean final hardness of 16.1 to 22.2 kp (158 to 218 Newtons).

Example 2

Sustained release oral dosage form tablets having the ingredients shown in Table 1 were prepared using another process according to the following steps. Compound (1), dibasic calcium phosphate, glyceryl behenate, talc, and colloidal silicon dioxide were weighed out, screened through a #20 mesh screen and mixed in a V-blender for 15 minutes. The compaction portion of the sodium lauryl sulfate was weighed and passed through a #30 mesh screen. The compaction portion of the magnesium stearate was weighed and passed through a #40 mesh screen. Screened sodium lauryl sulfate and magnesium stearate were added to the V-blender and blended for 5 minutes. The blend was discharged and compressed into compacts on a Chilsonator (roller compactor by FitzPatrick, Elmhurst, Ill.) machine. The obtained compacts were then passed through a hammer mill (FitzPatrick, Elmhurst, Ill.) to obtain the milled material for further compression. The tableting portion of the sodium lauryl sulfate was weighed and passed through a #30 mesh screen. The tableting portion of the magnesium stearate was weighed and passed through a #40 mesh screen. The milled material and the tableting portions of the sodium lauryl sulfate and magnesium stearate were added to the V-blender and blended for 3 minutes. The blended material was discharged and compressed to form tablets having a total weight of 1310 mg and a compound (1) loading of 600 mg (45.8 wt %). The blend was also compressed into 655 mg tablets having a compound (1) loading of 300 mg. The tablets had a mean final hardness of 15.7 to 18.9 kp and 11.1 to 13.7 kp, respectively.

Example 3

A randomized, crossover, fed/fasted single-dose study of the safety, tolerability, and pharmacokinetics of an sustained release oral dosage form of compound (1) in healthy adult patients was conducted. Sustained release oral dosage forms of Example 1 were used. The study was designed to evaluate the performance of this formulation in humans in comparison with a commercial gabapentin capsule formulation (Neurontin®). Twelve healthy adult volunteers (7 males and 5 females) participated in the study. Mean body weight was 75.6 kg. All patients received two different treatments in a random order with a one-week washout between treatments. The two treatments were: A) a single oral dose of Example 1 tablets (2×600 mg compound (1)) after an overnight fast; and B) a single oral dose of Example 1 tablets (2×600 mg compound (1)) after a high fat breakfast.

Blood and plasma samples were collected from all patients prior to dosing, and at 0.5, 1, 1.5, 2, 3, 4, 6, 8, 12, 18, 24, and 36 hours after dosing. Urine samples were collected from all patients prior to dosing, and complete urine output was obtained at the 0-4, 4-8, 8-12, 12-18, 18-24, and 24-36 hour intervals after dosing. Blood samples were quenched immediately with methanol and stored frozen at ≤70° C. Sample aliquots were prepared for analysis of gabapentin and compound (1) using sensitive and specific LC/MS/MS methods.

The plasma concentration ±1 SD of gabapentin following oral dosing of sustained release oral dosage forms prepared according to Example 1 to fasted and fed healthy adult patients is shown in FIGS. 1 and 2, respectively.

The mean±SD $C_{max}$ for gabapentin in plasma after oral dosing of the tablets (fasted) was 4.21±1.15 μg/mL. Following administration of the tablets after a high fat breakfast, the $C_{max}$ of gabapentin in plasma was further increased to 6.24±1.55 μg/mL. The mean±SD AUC for gabapentin in plasma after oral dosing of the tablets (fasted) was 54.5±12.2 μg·hr/mL. Following administration of the tablets after a high fat breakfast, the AUC of gabapentin in plasma was further increased to 83.0±21.8 μg·hr/mL. In the presence of food, exposure to gabapentin after oral administration of the tablets increased an additional 52% compared to that in fasted patients.

The time to peak plasma concentration ($T_{max}$) of gabapentin was significantly delayed after oral administration of the tablets. In fasted patients, oral administration of the tablets gave a gabapentin $T_{max}$ of 5.08±1.62 hr. This compares to a typical $T_{max}$ of immediate release gabapentin of about 2-4 hrs. The gabapentin $T_{max}$ after oral administration of the tablets was further delayed to 8.40±2.07 hr in the presence of food. The apparent terminal elimination half-life for gabapentin in plasma was similar for all treatments: 6.47±0.77 hr for the tablets in fasted patients, and 5.38±0.80 hr for the tablets in fed patients.

Following oral administration of the tablets, the percent of the gabapentin dose recovered in urine was 46.5±15.8% for fasted patients and 73.7±7.2% for fed patients.

Exposure to intact prodrug in plasma after oral administration of the tablets was low. After oral dosing of the tablets in fasted patients, concentrations of intact compound (1) in plasma reached a maximum of 0.040 μg/mL, approximately 1.0% of the corresponding peak gabapentin concentration. Similarly, the AUC of compound (1) in plasma of these patients was 0.3% of the corresponding AUC of gabapentin in plasma. After oral dosing of the tablets in fed patients, concentrations of intact compound (1) in plasma reached a maximum of 0.018 μg/mL, approximately 0.3% of the corresponding peak gabapentin concentration. Similarly, the AUC of compound (1) in plasma of these patients was <0.1% of the AUC of gabapentin in plasma.

Example 4

Figure 3:
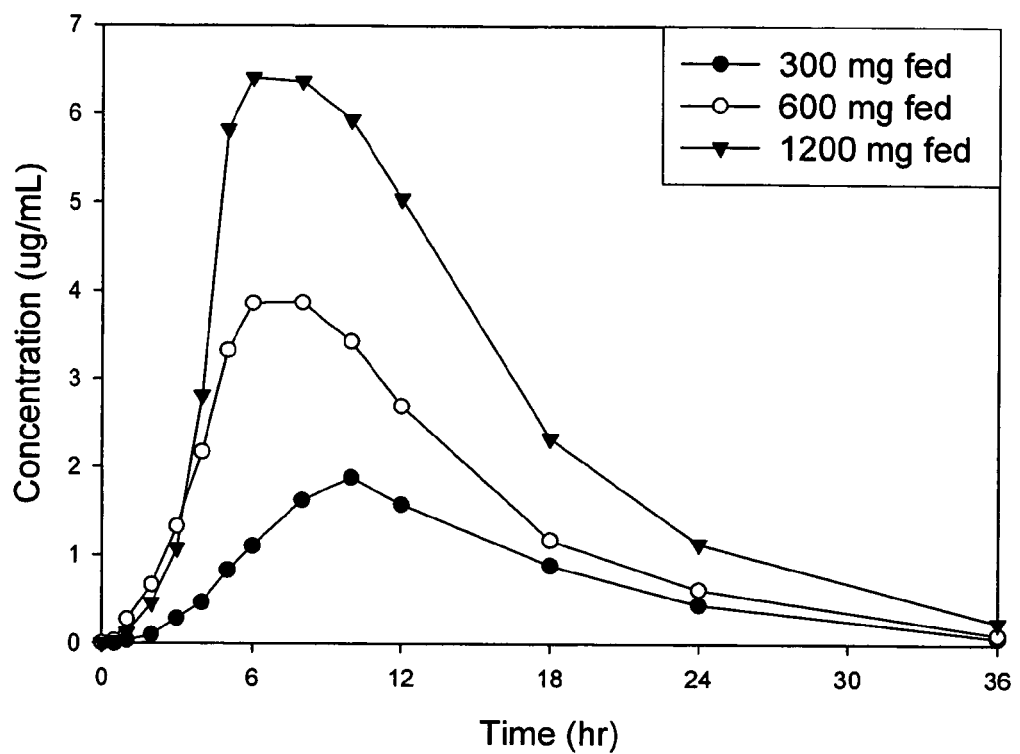
FIG. 3 is a graph of mean concentrations of gabapentin in plasma after oral administration of sustained release tablets containing compound (1) (1×300 mg; 1×600 mg; and 2×600 mg) to fed patients (Treatment B) as described in Example 4.

The mean plasma concentration of gabapentin following oral dosing of sustained release oral dosage forms prepared according to Example 2 to fed human patients is shown in FIG. 3. The mean plasma concentration of gabapentin in 12 human patients was determined according to the method disclosed in Example 3 following administration of (a) one tablet comprising 300 mg of compound (1), (b) one tablet comprising 600 mg of compound (1), and (c) 1200 mg of compound (1) in two tablets, each tablet comprising 600 mg of compound (1).

Example 5

Figure 4:
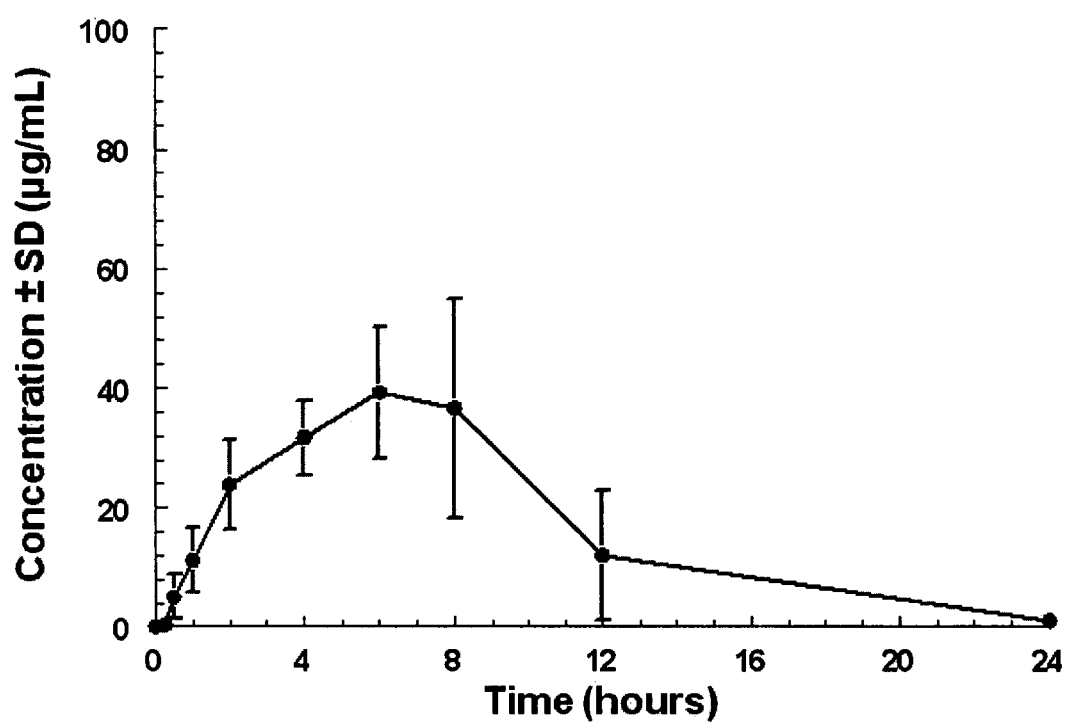
FIG. 4 is a graph of mean concentrations ±SD of gabapentin in blood after oral administration of a sustained release tablet containing compound (1) (1×600 mg) to fasted adult male Cynomologous monkeys as described in Example 5.

The blood concentration ±1 SD of gabapentin following oral dosing of sustained release oral dosage forms prepared according to Example 1 to Cynomologous monkeys is shown in FIG. 4. Blood concentration of gabapentin in Cynomologous monkeys was determined according to the following procedure.

Administration Protocol

Tablets comprising compound (1) (1×600 mg compound (1) per tablet) were administered by oral dosing to groups of four adult male Cynomologous (*Macaca fascicularis*) monkeys (weight about 3 kg). Each monkey was administered one tablet. Animals were fasted overnight before the study and for 4 hours post-dosing. Blood samples (1.0 mL) were obtained via the femoral vein at intervals over 24 hours after oral dosing. Blood was immediately quenched using methanol and frozen at −20° C. until analyzed. Test compounds were administered in the monkeys with a minimum of 72-hour wash out period between dosing sessions.

Sample Preparation for Absorbed Drug

300 μL of methanol was added to 1.5 mL Eppendorf tubes for the preparation of samples and standards.

Sample Preparation: Blood was collected at different time points and immediately 100 μL of blood was added into Eppendorf tubes containing 300 μL of methanol and mixed by vortexing.

Standard Preparation: Ninety μL of blood was added to 300 μL of methanol in Eppendorf tubes. 10 μL of gabapentin standard solution (0.04, 0.2, 1, 5, 25, and 100 μg/mL) was added to each tube to make up the final calibration standards (0.004, 0.02, 0.1, 0.5, 2.5, and 10 μg/mL).

20 μL of p-chlorophenylalanine was added to all samples and standards.

The samples were vortexed and centrifuged at 14,000 rpm for 20 min.

The supernatant was used for LC/MS/MS analysis.

LC/MS/MS Analysis

The concentration of gabapentin in monkey blood was determined using an API 2000 LC/MS/MS instrument equipped with a Shimadzu SCL-10AVP and LEAP autosampler. The column was a Zorbax C8XDB 4.6×150 mm column operating at room temperature. The mobile phases were (A) 0.1% formic acid in water, and (B) 0.1% formic acid in acetonitrile. The gradient condition was: 2% B for 3.5 min, increasing to 95% B in 3.5 min and maintained for 2 min, then decreasing to 2% B in 5.6 min and maintained for 2.3 min. 30 μL of sample was injected into the column. A Turbo-IonSpray source was used, and gabapentin was detected in positive ion mode for the MRM transition of 172/137. Peaks were integrated using Analyst 1.2 quantitation software.

Example 6

Sustained release oral dosage form tablets containing compound (1) were made having the ingredients shown in Table 2:

TABLE 2

| Ingredient | Manufacturer | Amount/Tablet (mg/tablet) | Composition (wt %) | Ingredient Category |
|---|---|---|---|---|
| Compound (1) | XenoPort (Santa Clara, CA) | 600.00 | 54.55 | Prodrug |
| Microcrystalline Cellulose PH113, USP | FMC (Philadelphia, PA) | 143.60 | 13.05 | Diluent |
| Glyceryl Behenate, NF | Gattefosse (Saint Pirest, Cedex, France) | 262.02 | 23.82 | Lubricant/Release controlling agent |
| Talc, USP | Barrett Minerals (Mount Vernon, IN) | 56.43 | 5.13 | Anti-adherent |
| Colloidal Silicon Dioxide, NF | Cabot (Tuscola, IL) | 3.74 | 0.34 | Glidant |
| Sodium Dodecyl Sulfate, NF | Fisher (Fairlawn, NJ) | 8.47 | 0.77 | Surfactant (first portion) |
| Magnesium Stearate, NF | Mallinckrodt (Phillipsburg, NJ) | 11.33 | 1.03 | Lubricant (first portion) |
| Sodium Dodecyl Sulfate, NF | Fisher (Fairlawn, NJ) | 10.12 | 0.92 | Surfactant (second portion) |
| Magnesium Stearate, NF | Mallinckrodt (Phillipsburg, NJ) | 4.29 | 0.39 | Lubricant (second portion) |
| Total | | 1100.00 | 100 | |

The tablets were made according to the following steps. Compound (1), microcrystalline cellulose (MCC PHI 13), glyceryl behenate, talc, colloidal silicon dioxide, and sodium dodecyl sulfate (SDS) (first blending portion) and magnesium stearate (first blending portion) were weighed out, screened through a #20 mesh screen and mixed in a V-blender for 7 minutes (MaxiBlend Lab Blender MB-1 (Globepharma)). The blended ingredients were poured into the feed hopper of a roller compactor (BO50PH Compactor, cropped roll/closed end, 3.9-in roll diameter, 1.5-in roll width, 11.6 kN roll force, 12 rpm roll speed and 7 rpm horizontal screw feed speed). The compacted material was then passed through a Quadro Underdriven Comil Model U5 mill (Quadro Engineering, Inc., Millburn, N.J., 0.079-in grater hole size, 1607 impeller style, 2500 impeller rpm)) to obtain milled material for further compression. The milled material was transferred to a blender (MaxiBlend Lab Blender model MB-1 (Globepharma), 25 rpm shell speed) and mixed for 5 minutes. Additional SDS (second blending portion) and/or magnesium stearate (second blending portion) was added as necessary to achieve the specified amounts. The blended material was discharged and compressed to form tablets having a total weight of 1100 mg and a compound (1) loading of 600 mg (54.55 wt %). The tablets had a mean final hardness of 14 to 17 kp (137 to 214 Newtons).

Example 7

Figure 5:
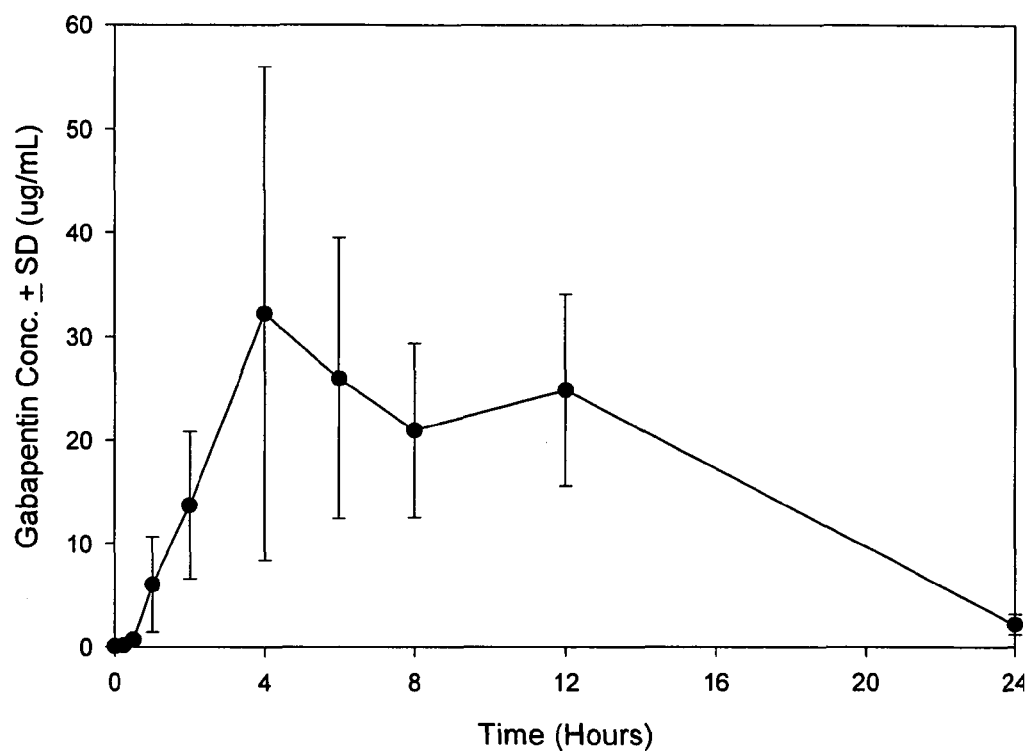
FIG. 5 is a graph of mean concentrations ±SD of gabapentin in blood after oral administration of a sustained release tablet containing compound (1) (1×600 mg) to fasted adult male Cynomologous monkeys as described in Example 7.

The blood concentration ±1 SD of gabapentin following oral dosing of a sustained release oral dosage form (1×600 mg) prepared according to Example 6 to Cynomologous monkeys is shown in FIG. 5. The blood concentration of gabapentin in Cynomologous monkeys was determined according to the method disclosed in Example 5.

Example 8

The following steps were used to determine the in vitro dissolution profile of dosage forms prepared according to Examples 1, 2, and 6. A dosage form was placed into a dissolution vessel containing 900 mL of 10 mM monobasic potassium phosphate buffer ($KH_2PO_4$, pH 7.4) and 1% (wt/volume) sodium lauryl sulfate at 37° C. The dissolution medium was agitated at 50 rpm (USP, Type II, paddle). Samples were withdrawn at 0.5, 1, 2, 4, 6, 8, 12, and 24 hours and the content of compound (1) in solution was determined by reverse phase HPLC using a C 18 column and a phosphate buffer/acetonitrile/water isocratic mobile phase with photodiode detection at 210 nm.

Figure 6:
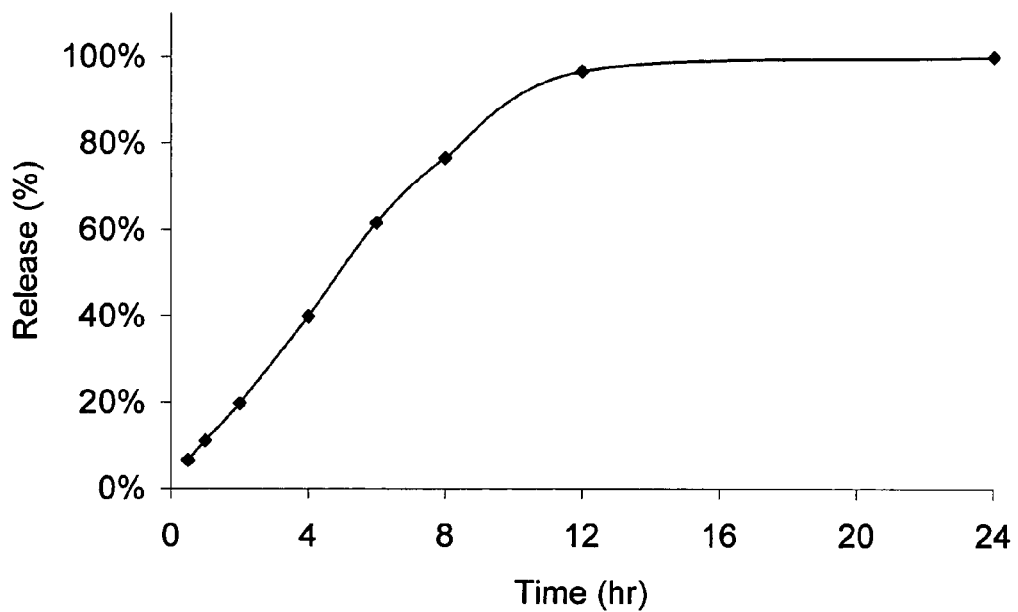
FIG. 6 shows an in vitro dissolution profile of a dosage form of the present disclosure prepared as described in Example 1.
Figure 7A:
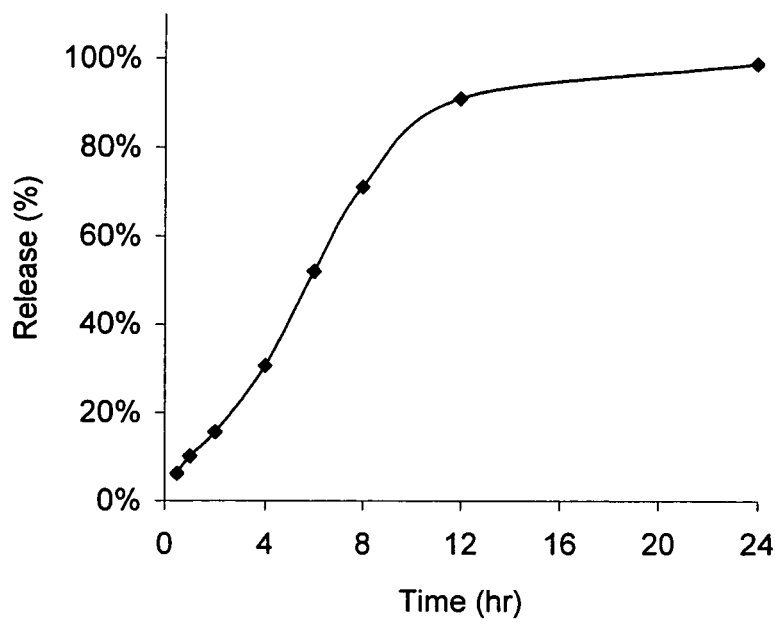
FIGS. 7A and 7B shows in vitro dissolution profiles of other dosage forms of the present disclosure prepared as described in Example 2.
Figure 7B:
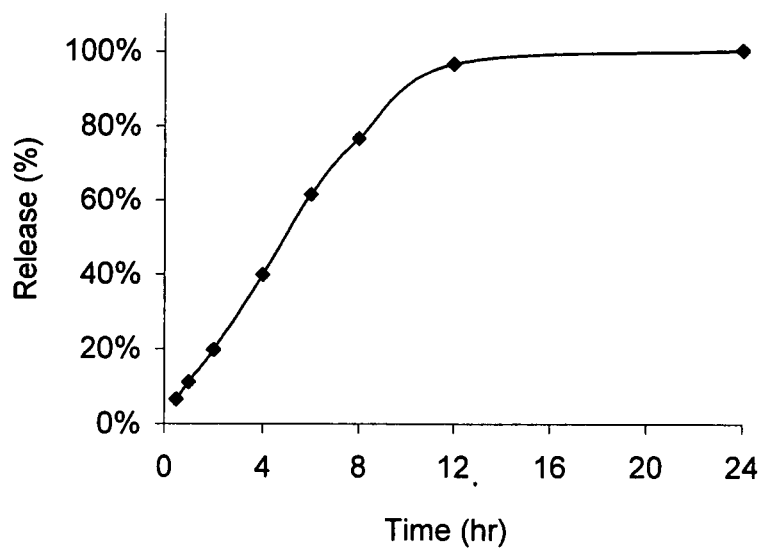
Figure 8:
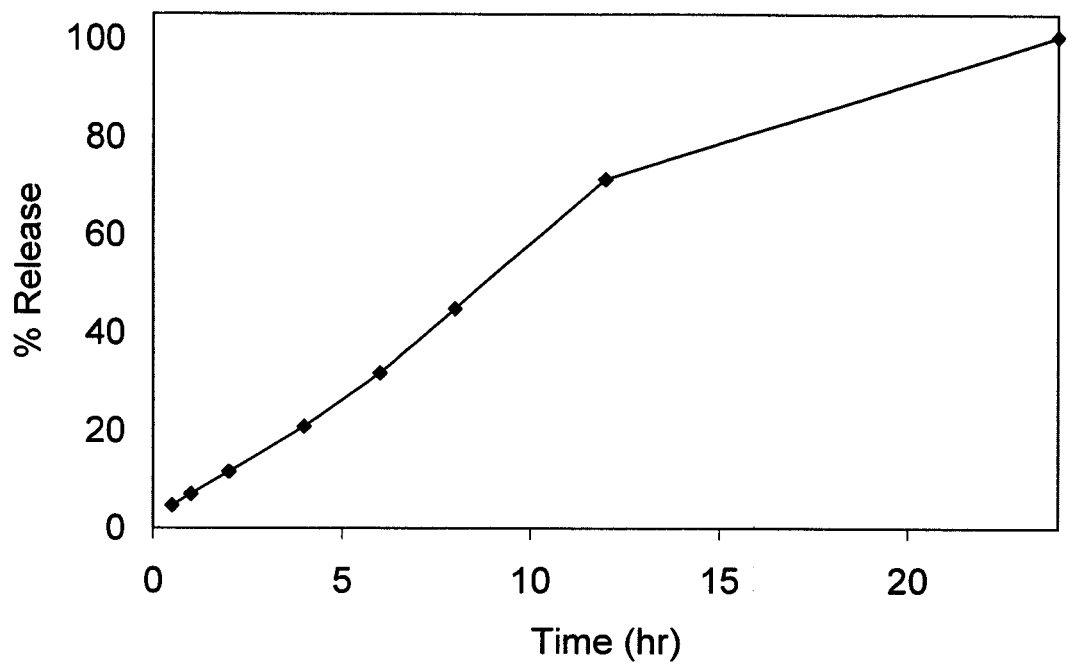
FIG. 8 shows an in vitro dissolution profile of another dosage form of the present disclosure prepared as described in Example 6.

As shown in FIG. 6, dosage forms prepared according to Example 1 released about 20% of compound (1) after about 2 hours, about 50% after about 5 hours, and about 80% after about 8 hours. As shown in FIG. 7A, dosage forms comprising 300 mg of compound (1) prepared according to Example 2 released about 20% of compound (1) after about 2 hours, about 50% after about 6 hours, and about 80% after about 10 hours. As shown in FIG. 7B, dosage forms comprising 600 mg of compound (1) prepared according to Example 2 released about 20% of compound (1) after about 2 hours, about 50% after about 5 hours, and about 80% after about 8 hours. As shown in FIG. 8, dosage forms prepared according to Example 6 released about 30% of compound (1) after about 5 hours, about 60% after about 10 hours, and about 80% after about 15 hours.

Finally, it should be noted that there are alternative ways of implementing the present invention. Accordingly, the present embodiments are to be considered as illustrative and not restrictive, and the invention is not to be limited to the details given herein, but may be modified within the scope and equivalents of the claim(s) issuing here from.

All publications and patents cited herein are incorporated by reference in their entirety.

What is claimed is:

1. A sustained release oral tablet comprising:
   (a) 40 wt % to 65 wt % of 1-{[(α-isobutanoyloxyethoxy) carbonyl]aminomethyl}-1-cyclohexane acetic acid;
   (b) 1 wt % to 30 wt % of glyceryl behenate; and
   (c) 30 wt % to 50 wt % of dibasic calcium phosphate;
   wherein wt % is based on the total dry weight of the dosage form, which tablet:
   when administered to one or more fasted human patients at a dose of 1-{[(α-isobutanoyloxyethoxy)carbonyl]aminomethyl}-1-cyclohexane acetic acid ranging from 1100 mg to 1300 mg provides a gabapentin plasma concentration profile characterized by a $C_{max}$ ranging from 3 μg/mL to 6 μg/mL, a $T_{max}$ ranging from 4 hours to 7 hours, and an AUC ranging from 30 μg·hr/mL to 70 μg·hr/mL; or
   when administered to one or more fed human patients at a dose of 1-{[(α-isobutanoyloxyethoxy)carbonyl]aminomethyl}-1-cyclohexane acetic acid ranging from 1100 mg to 1300 mg provides a gabapentin plasma concentration profile characterized by a $C_{max}$ ranging from 5 μg/mL to 8 μg/mL, a $T_{max}$ ranging from 6 hours to 11 hours, and an AUC ranging from 60 μg·hr/mL to 110 μg·hr/mL.

2. The tablet of claim 1, which is compressed to a hardness of at least 15 kiloponds.

3. The tablet of claim 1, comprising an amount of 1-{[(α-isobutanoyloxyethoxy)carbonyl]aminomethyl}-1-cyclohexane acetic acid ranging from 300 mg to 700 mg.

4. The tablet of claim 1, wherein the 1-{[(α-isobutanoyloxyethoxy)carbonyl]aminomethyl}-1-cyclohexane acetic acid is in a crystalline form.

5. The tablet of claim 1, comprising one or more pharmaceutically acceptable excipients selected from diluents, lubricants, anti-adherents, glidants, surfactants, disintegrants, and combinations of any of the foregoing.

6. The tablet of claim 5, wherein the diluent is microcrystalline cellulose.

7. The tablet of claim 1, wherein the tablet comprises 600 mg of 1-{[(α-isobutanoyloxyethoxy)carbonyl]aminomethyl}-1-cyclohexane acetic acid, and the dose comprises two of the tablets.

8. The tablet of claim 1, comprising a coating.

9. The tablet of claim 1, which
   when administered to the one or more fasted human patients at a dose of 1-{[(α-isobutanoyloxyethoxy)carbonyl]aminomethyl}-1-cyclohexane acetic acid ranging from 1100 mg to 1300 mg provides a gabapentin plasma concentration profile characterized by a $C_{max}$ ranging from 3 μg/mL to 6 μg/mL, a $T_{max}$ ranging from 4 hours to 7 hours, and an AUC ranging from 30 μg·hr/mL to 70 μg·hr/mL; and
   when administered to the one or more fed human patients at a dose of 1-{[(α-isobutanoyloxyethoxy)carbonyl]aminomethyl}-1-cyclohexane acetic acid ranging from 1100 mg to 1300 mg provides a gabapentin plasma concentration profile characterized by a $C_{max}$ ranging from 5 μg/mL to 8 μg/mL, a $T_{max}$ ranging from 6 hours to 11 hours, and an AUC ranging from 60 μg·hr/mL to 110 μg·hr/mL.

10. The tablet of claim 1, which
    when administered to a population of said fasted human patients at a dose of 1-{[(α-isobutanoyloxyethoxy)carbonyl]aminomethyl}-1-cyclohexane acetic acid ranging from a 1100 mg to 1300 mg provides a gabapentin plasma concentration profile characterized by a mean $C_{max}$ ranging from 3 μg/mL to 6 μg/mL, a mean $T_{max}$ ranging from 4 hours to 7 hours, and a mean AUC ranging from 30 μg·hr/mL to 70 μg·hr/mL; and
    when administered to a population of said fed human patients at a dose of 1-{[(α-isobutanoyloxyethoxy)carbonyl]aminomethyl}-1-cyclohexane acetic acid ranging from 1100 mg to 1300 mg provides a gabapentin plasma concentration profile characterized by a mean $C_{max}$ ranging from 5 μg/mL to 8 μg/mL, a mean $T_{max}$ ranging from 6 hours to 11 hours, and a mean AUC ranging from 60 μg·hr/mL to 110 μg·hr/mL.

11. The tablet of claim 1, wherein:
    the one or more fasted human patients do not eat any food from 10 hours prior to administering the dose until 4 hours after dosing, drink 250 mL of water 2 hours and 1 hour prior to dosing and 250 mL of water a 2 hours after dosing, eat a lunch 4 hours after dosing, and eat a dinner 10 hours after dosing; and
    the one or more fed human patients begin eating a test meal 30 minutes prior to administering the dose and complete eating the test meal 5 minutes prior to administering the dose, eat a lunch 4 hours after dosing, and eat a dinner 10 hours after dosing, wherein the test meal comprises 1000 total calories of which 500 calories comprise fat calories.

12. A sustained release oral tablet comprising:
    (a) 40 wt % to 65 wt % of 1-{[(α-isobutanoyloxyethoxy) carbonyl]aminomethyl}-1-cyclohexane acetic acid;
    (b) 1 wt % to 30 wt % of glyceryl behenate; and
    (c) 30 wt % to 50 wt % of dibasic calcium phosphate;
    wherein wt % is based on the total dry weight of the tablet, which tablet when placed in 10 mM monobasic potassium phosphate buffer and 1% (wt/volume) sodium lauryl sulfate at pH 7.4 and 37° C. agitated at 50 rpm (USP, Type II), releases 20% of the 1-{[(α-isobutanoyloxyethoxy)carbonyl]aminomethyl}-1-cyclohexane acetic acid after 2 hours, 50% after 5 hours, and 80% after 8 hours.

13. The tablet of claim 12, comprising an amount of 1-{[(α-isobutanoyloxyethoxy)carbonyl]aminomethyl}-1-cyclohexane acetic acid ranging from 500 mg to 700 mg.

14. The sustained release oral tablet according to claim 1, further comprising: 5 wt % to 20 wt % of microcrystalline cellulose.

15. The tablet of claim 14, comprising an amount of 1-{[(α-isobutanoyloxyethoxy)carbonyl]aminomethyl}-1-cyclohexane acetic acid ranging from 500 mg to 700 mg.

16. A sustained release oral tablet, comprising:
    45.8 wt % 1-{[(α-isobutanoyloxyethoxy)carbonyl]aminomethyl}-1-cyclohexane acetic acid;
    39.56 wt % dibasic calcium phosphate;
    4.58 wt % glyceryl behenate;
    6.11 wt % talc;
    0.41 wt % colloidal silicon dioxide;
    1.84 wt % sodium lauryl sulfate; and
    1.69 wt % magnesium stearate;
    which tablet is optionally coated.

17. The tablet of claim 16, comprising 300 mg to 700 mg 1-{[(α-isobutanoyloxyethoxy)carbonyl]aminomethyl}-1-cyclohexane acetic acid.

18. A method of treating restless legs syndrome, comprising administering a tablet according to one of claims 1, 12, or 16, to a patient in need of such treatment.

19. A method of treating post-herpetic neuralgia, comprising administering a tablet according to one of claims 1, 12, or 16, to a patient in need of such treatment.

* * * * *